United States Patent
Muramoto

[11] Patent Number: 5,084,244
[45] Date of Patent: Jan. 28, 1992

[54] ARTIFICIAL LUNG ASSEMBLY

[75] Inventor: Tomonori Muramoto, Fujinomiya, Japan

[73] Assignee: Terumo Kabushiki Kaisha, Tokyo, Japan

[21] Appl. No.: 715,037

[22] Filed: Jun. 12, 1991

Related U.S. Application Data

[63] Continuation of Ser. No. 460,276, Jan. 2, 1990, abandoned.

[30] Foreign Application Priority Data

Jan. 10, 1989 [JP] Japan ..................... 1-3519

[51] Int. Cl.$^5$ .............................. A61M 1/18
[52] U.S. Cl. ........................ 422/46; 422/48; 128/DIG. 3; 261/DIG. 28; 210/321.81; 210/321.9; 210/512.1
[58] Field of Search ............. 422/46, 48; 128/DIG. 3; 261/DIG. 28; 210/321.81, 321.9, 512.1

[56] References Cited

U.S. PATENT DOCUMENTS

| | | | |
|---|---|---|---|
| Re. 32,186 | 6/1986 | Bentley | 210/646 |
| 4,141,835 | 2/1979 | Schael et al. | 210/456 X |
| 4,240,907 | 12/1980 | Bentley | 210/646 |
| 4,376,095 | 3/1983 | Hasegawa | 422/48 X |
| 4,657,743 | 4/1987 | Kanno | 422/46 |
| 4,690,762 | 9/1987 | Katsura | 210/436 |
| 4,919,802 | 4/1990 | Katsura | 210/188 |

FOREIGN PATENT DOCUMENTS

| | | |
|---|---|---|
| 0081118 | 6/1983 | European Pat. Off. |
| 0257279 | 3/1988 | European Pat. Off. |
| 0264696 | 4/1988 | European Pat. Off. |
| 53-49896 | 5/1978 | Japan |
| 57-86361 | 5/1982 | Japan |
| 60-5308 | 2/1985 | Japan |
| 62-211072 | 9/1987 | Japan |
| 63-43672 | 2/1988 | Japan |
| 63-104617 | 5/1988 | Japan |

Primary Examiner—Lynn Kummert
Attorney, Agent, or Firm—Frishauf, Holtz, Goodman & Woodman

[57] ABSTRACT

An artificial lung includes a housing having gas inlet and outlet ports, a blood inlet chamber mounted on the upper ends of the housing, a blood outlet chamber mounted on the lower end of the housing, and a plurality of hollow fiber membranes for exchanging a gas, disposed within the housing and having ends opening into the blood inlet chamber and opposite ends opening into the blood outlet chamber. A blood inlet port communicates with the blood inlet chamber and is positioned such that the ratio of the distance from the central axis of the blood inlet chamber to the central axis of the blood inlet port to the inside radius of the blood inlet chamber ranges from 0.25 to 0.95, so that blood introduced from the blood inlet port into the blood inlet chamber will be swirled in one direction.

6 Claims, 8 Drawing Sheets

| Method of introducing blood | Inventive Example 2 Swirled, offset ratio 10mm offset value 0.28 | Inventive Example 3 Swirled, offset ratio 25mm offset value 0.71 | Inventive Example 4 Swirled, offset ratio 33mm offset value 0.93 |
|---|---|---|---|
| Blood flow pattern | | | |
| Dwell time (sec) | 4.0 | 5.0 | 5.6 |
| Number of Samples | n=5 | n=5 | n=5 |

| Method of introducing blood | Comparative Example 3 straight | Comparative Example 4 slanted | Comparative Example 5 Swirled, offset ratio 25mm offset value 0.99 |
|---|---|---|---|
| Blood flow pattern | | | |
| Dwell time (sec) | 7.3 | 5.2 | 6.1 |
| Number of Samples | n=5 | n=5 | n=5 |

ARTIFICIAL LUNG ASSEMBLY

This application is a continuation of application Ser. No. 07/460,276, filed Jan. 2, 1990, now abandoned.

BACKGROUND OF THE INVENTION

The present invention relates to an artificial lung which employs hollow fiber membranes, and more particularly to an artificial lung which includes a cylindrical housing with hollow fiber membranes disposed therein, the cylindrical housing having a blood inlet port which is displaced from the longitudinal axis of the housing so that blood introduced from the blood inlet port into the housing is swirled therein and air bubbles produced in the blood are reduced.

When a surgical operation is effected on the chest of a patient, an extracorporeal blood circulation circuit including an artificial lung, also known as an oxygenator, is used in recent years in bypassing relation to the lung of the patient, and carbon dioxide is removed from the blood of the patient and fresh oxygen is added to the blood by the artificial lung. The artificial lung in the extracorporeal blood circulation circuit employs hollow fiber membranes which can be small in size and of a rugged structure, and exchange gases stably at a high rate and are easy to handle.

Figure 1:
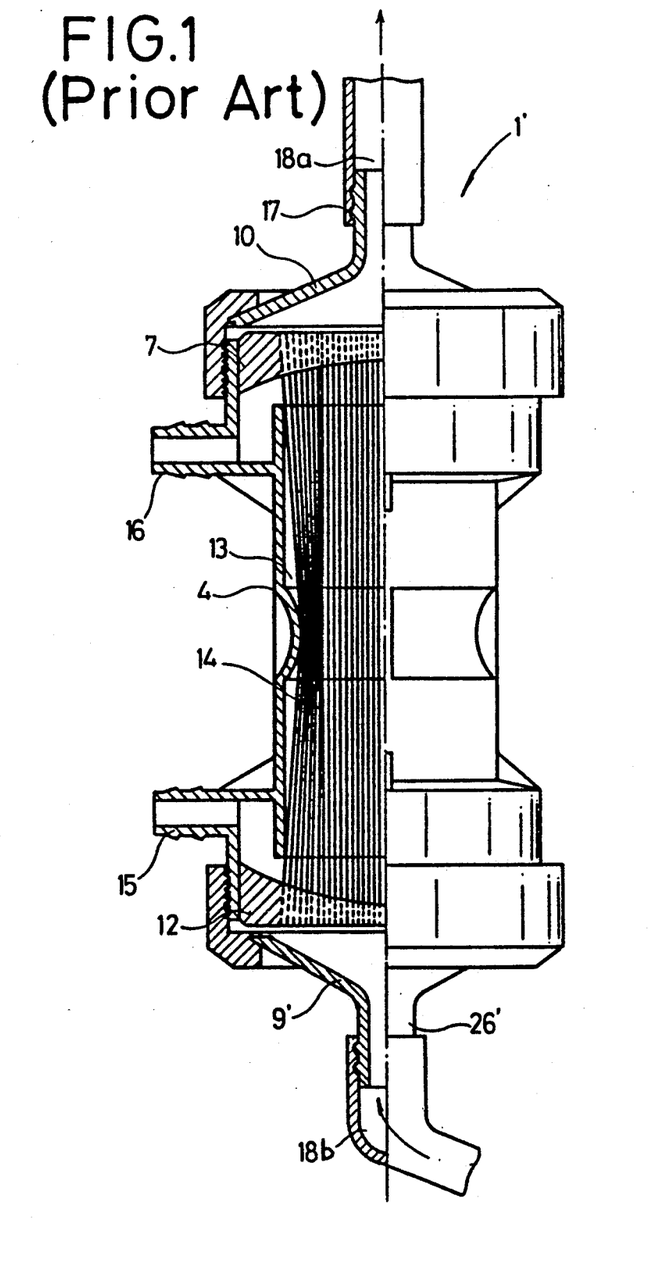
FIGS. 1 and 2 are partly sectional side elevational views of conventional artificial lungs.

One conventional artificial lung which incorporates hollow fiber membranes is shown in FIG. 1 of the accompanying drawings.

As shown in FIG. 1, the artificial lung, generally denoted at 1', comprises a cylindrical housing 4 which has a gas outlet port 15 and a gas inlet port 16, a blood outlet cover 10 mounted on the upper end of the housing 4 with a first partition 7 disposed therebetween, a blood inlet cover 9' mounted on the lower end of the housing 4 with a second partition 12 disposed therebetween, and a plurality of hollow fiber membranes 14 placed in the housing 4, for exchanging gases, the hollow fiber membranes 14 having upper ends opening into the blood outlet cover 10 and lower ends opening into the blood inlet cover 9'. The gas-exchanging hollow fiber membranes 14 extend substantially parallel to each other in the housing 4.

Each of the hollow fiber membranes 14 has a hollow space extending axially therethrough and also has a multiplicity of small holes (not shown) defined in its circumferential wall and extending radially between inner and outer wall surfaces. The hollow fiber membranes 14 may be made of a hydrophobic synthetic resin such as polypropylene. Alternatively, the hollow fiber membranes 14 may be made as porous hollow fiber membranes of a hydrophilic synthetic resin, and the inner wall surfaces thereof may be rendered hydrophobic by a silicone oil film coated thereon.

The opposite ends of the hollow fiber membranes 14 are supported in a fluid-tight fashion by the first and second partitions 7, 12, which are made of polyurethane or the like. The partitions 7, 12 divide the housing 4, the blood inlet cover 9', and the blood outlet cover 10 from each other in a fluid-tight manner, and define a gas chamber 13 therebetween within the housing 4.

Blood outlet and inlet ports 17, 26, are connected to the blood outlet and inlet cover 10, 9', respectively, and extend in the axial direction of the hollow fiber membranes 14 so that any localized flow of blood in the artificial lung 1' will be reduced. The blood outlet and inlet ports 17, 26' are joined to tubes 18a, 18b, respectively, of the extracorporeal blood circulation circuit. The hollow fiber membranes 14 of the artificial lung 1' are generally directed axially vertically so that blood will be distributed uniformly in the extracorporeal blood circulation circuit and any water which has been condensed on the outer wall surfaces of the hollow fiber membranes 14 will flow downwardly. The blood outlet port 17 is disposed at the lower end of the artificial lung 1'. Therefore, blood which flows into the blood inlet port 26' is directed upwardly, passes upwardly through the hollow fiber membranes 14 in the housing 4, and then flows out of the blood outlet port 17. The artificial lung 1' is located in the lowest position in the extracorporeal blood circulation circuit in order to prevent small air bubbles from being mixed into the blood because of air which enters the hollow fiber membranes 14, when the pressure of the blood in the extracorporeal blood circulation circuit is lowered at the time the circuit is primed or while the blood is circulating through the circuit.

However, since the blood outlet and inlet ports 17, 26' are vertically disposed and the tube 18b should not be bent sharply, the artificial lung 1' cannot be sufficiently lowered in position in the extracorporeal blood circulation circuit. The pressure of the blood in the circuit is therefore relatively low, allowing air to enter the hollow fiber membranes 14 and to be trapped as small air bubbles in the blood.

Figure 2:
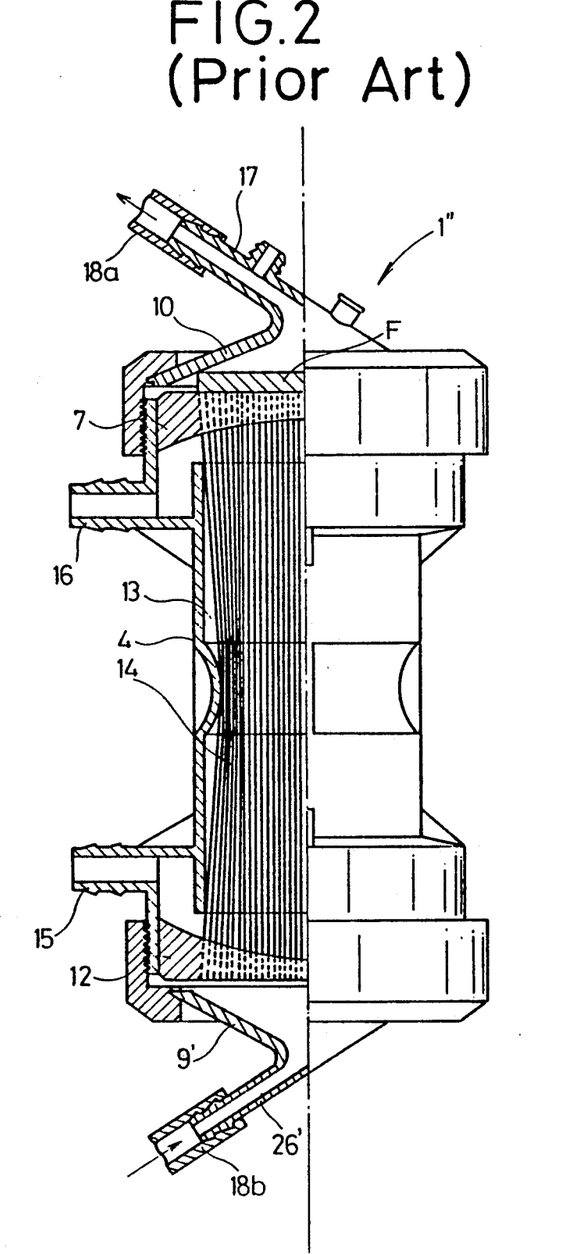

FIG. 2 of the accompanying drawings shows another known artificial lung, denoted at 1", which is designed to solve the problem of the above conventional artificial lung. The artificial lung 1" shown in FIG. 2 is disclosed in Japanese Utility Model Publication No. 61(1986)-10697. The artificial lung 1" has a blood inlet port 26' at the lower end thereof, the blood inlet port 26' being inclined at an angle ranging from 50° to 100° with respect to the axis of the hollow fiber membranes 14. A filter F which has a mesh size in the range of from 200 to 400 is disposed in the blood outlet cover 10 between the open ends of the hollow fiber membranes 14 and the blood outlet port 17. The artificial lung 1" can be lowered in position in the extracorporeal blood circulation circuit without the tube 18b being bent sharply. Inasmuch as the pressure of the blood in the circuit is relatively high, air is prevented from entering the hollow fiber membranes 14, and hence the danger of small air bubbles being trapped in the blood is reduced.

SUMMARY OF THE INVENTION

It is an object of the present invention to provide an artificial lung which is constructed to reduce air bubbles in blood, allows blood to be dispersed well for a uniform supply of blood, and can discharge produced air bubbles so that they will not be trapped in the blood.

Another object of the present invention is to provide an artificial lung comprising a housing having gas inlet and outlet ports, a first partition disposed in an upper end of the housing, a blood inlet chamber mounted on the upper end of the housing and defined above the first partition, a second partition disposed in a lower end of the housing, a blood outlet chamber mounted on the lower end of the housing and defined below the second partition, a plurality of hollow fiber membranes for exchanging a gas, disposed within the housing and having ends opening into the blood inlet chamber and opposite ends opening into the blood outlet chamber, and a blood inlet port communicating with the blood inlet chamber and positioned such that the ratio of the distance from the central axis of the blood inlet chamber to the central axis of the blood inlet port to the inside radius of the blood inlet chamber ranges from 0.25 to 0.95, so that blood introduced from the blood inlet port into the blood inlet chamber will be swirled in one direction.

Still another object of the present invention is to provide the artificial lung further including an air bleed port communicating with the blood inlet chamber.

Yet another object of the present invention is to provide the artificial lung wherein the air bleed port is positioned substantially axially centrally in the blood inlet chamber.

A further object of the present invention is to provide an artificial lung assembly comprising: an artificial lung comprising an artificial lung housing having gas inlet and outlet ports, a first partition disposed in an upper end of the artificial lung housing, a first blood inlet chamber mounted on the upper end of the artificial lung housing and defined above the first partition, a second partition disposed in a lower end of the artificial lung housing, a blood outlet chamber mounted on the lower end of the artificial housing and defined below the second partition, and a plurality of hollow fiber membranes for exchanging a gas, disposed within the artificial lung housing and having ends opening into the first blood inlet chamber and opposite ends opening into the blood outlet chamber; and a heat exchanger mounted on the upper end of the artificial lung housing, the heat exchanger comprising a heat exchanger housing having thermal-medium inlet and outlet ports, a third partition disposed in an upper end of the heat exchanger housing, a second blood inlet chamber mounted on the upper end of the heat exchanger housing and defined above the third partition, a fourth partition disposed in a lower end of the heat exchanger housing and facing into the first blood inlet chamber, a plurality of pipes for exchanging heat, disposed within the heat exchanger housing and having ends opening into the second blood inlet chamber and opposite ends opening into the first blood inlet chamber, and a blood inlet port communicating with the second blood inlet chamber and positioned such that the ratio of the distance from the central axis of the second blood inlet chamber to the central axis of the blood inlet port to the inside radius of the second blood inlet chamber ranges from 0.25 to 0.95, so that blood introduced from the blood inlet port into the second blood inlet chamber will be swirled in one direction.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 3:
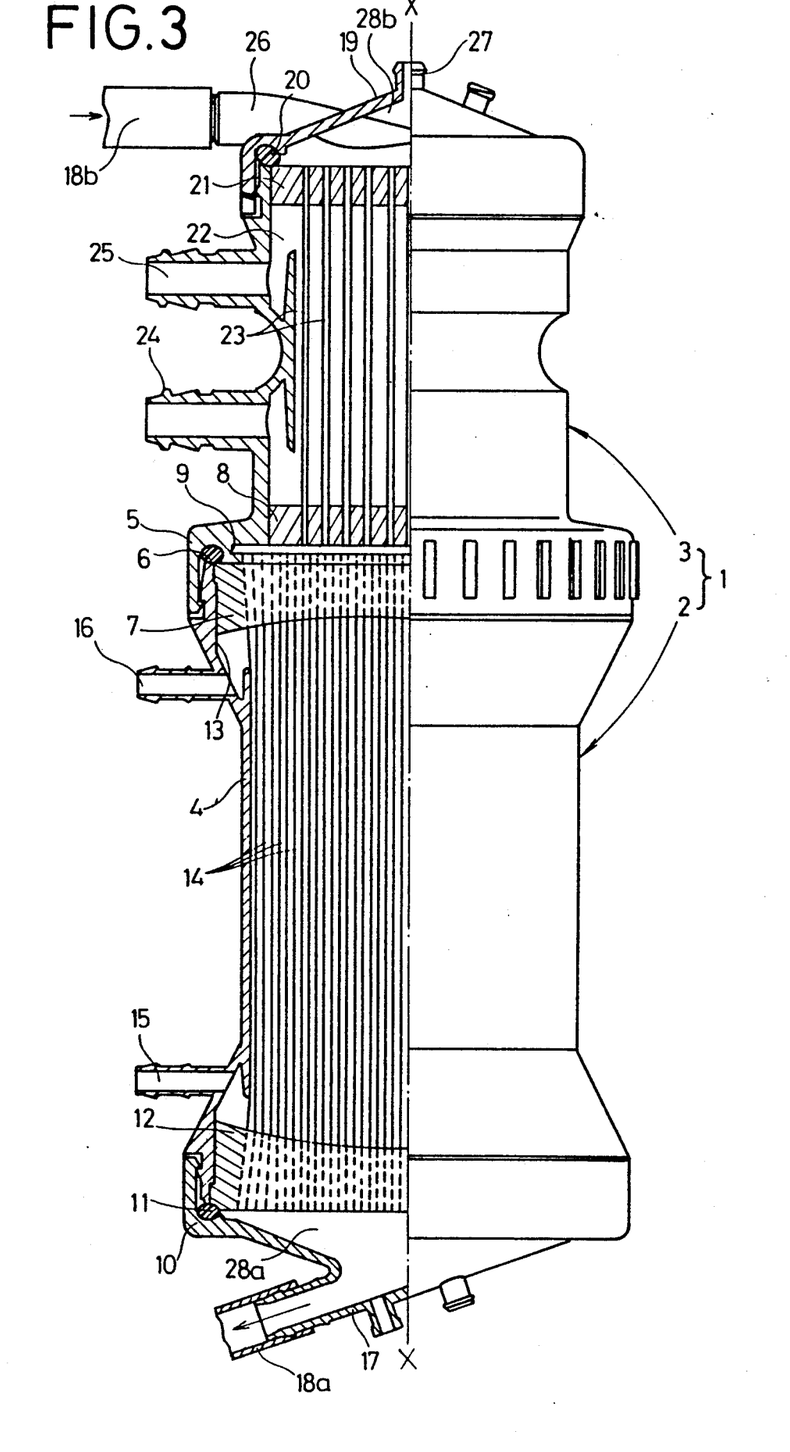
FIG. 3 is a partly sectional side elevational view of an artificial lung assembly according to the present invention, the artificial lung assembly comprising an artificial lung and a heat exchanger.

As shown in FIG. 3, an artificial lung or oxygenator assembly 1 basically comprises an artificial lung 2 and a heat exchanger 3 mounted on the upper end of the artificial lung 2. The artificial lung 2 has a cylindrical housing 4, and the heat exchanger 3 also has a cylindrical housing 5 which is hermetically fitted over the upper end of the housing 4 with an O-ring 6 interposed therebetween. A first partition 7 is hermetically fitted in the upper end of the housing 4. A fourth partition 8 is hermetically fitted in the lower end of the housing 5. The first and fourth partitions 7, 8 jointly define therebetween a blood inlet chamber 9 of the artificial lung 2. A blood outlet cover 10 is hermetically fitted over the lower end of the housing 4 with an O-ring 11 interposed therebetween. A second partition 12 is hermetically fitted in the lower end of the housing 4. The blood outlet cover 10 and the second partition 12 jointly define a blood outlet chamber 28a therebetween, which is separated from the interior space in the housing 4 by the lower partition 12. The first and second partitions 7, 12 jointly define a gas chamber 13 therebetween in the housing 4. The gas chamber 13 accommodates therein a plurality of hollow fiber membranes 14 for exchanging gases. The hollow fiber membranes 14 have upper and lower ends (as shown in FIG. 3) which extends through the first and second partitions 7, 12, respectively, and open into blood inlet chamber 9 and the blood outlet chamber 28a, respectively.

The hollow fiber membranes 14 are of the conventional nature. The housing 4 of the artificial lung 2 has axially spaced gas inlet and outlet ports 15, 16 which are defined in its outer circumferential wall and communicate with the gas chamber 13. The blood outlet cover 10 has a blood outlet port 17 with its axis inclined at a certain angle to the axial direction of the hollow fiber membranes 14. The axis of the blood outlet port 17 is inclined in order to prevent a tube 18a connected thereto from being sharply bent.

Figure 4A:
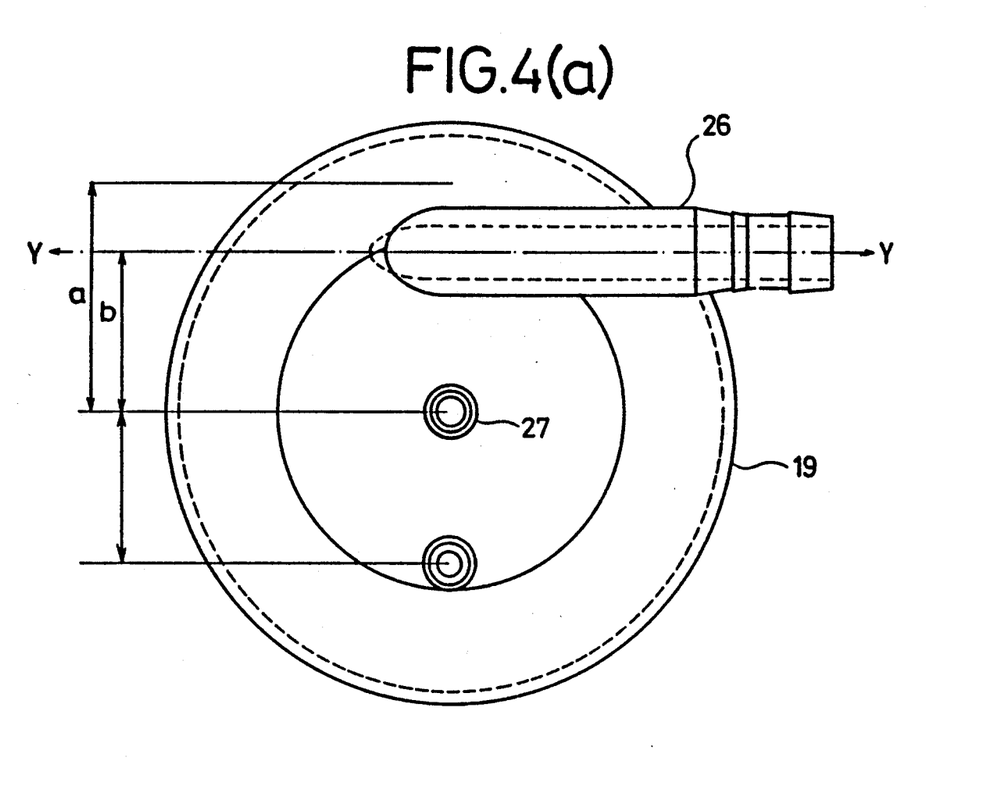
FIGS. 4(a) and 4(b) are enlarged plan and cross-sectional views, respectively, of a blood inlet cover of the heat exchanger.

The heat exchanger 3 has a blood inlet cover 19 which is hermetically fitted over the upper end of the housing 5 with an O-ring 20 interposed therebetween. A third partition 21 is hermetically fitted in the upper end of the housing 5. The blood inlet cover 19 and the third partition 21 jointly define a blood inlet chamber 28b, which is separated from the interior space in the housing 5 by the third partition 21. The third and fourth partitions 21, 8, jointly define a chamber 22 therebetween in the housing 5. The chamber 22 houses therein a plurality of heat-exchanging pipes 23 that extend axially in the housing 5. The pipes 23 have upper and lower ends (as shown in FIG. 3) extending through the third and fourth partitions 21, 8, respectively, and opening into the blood inlet chambers 28b, 9, respectively. The housing 5 has thermal medium (cold/warm water) inlet and outlet ports 24, 25 defined in its circumferential wall and axially spaced from each other, the inlet and outlet ports 24, 25 communicating with the chamber 22. The blood inlet cover 19 has a blood inlet port 26 which is positionally displaced radially outwardly from the central longitudinal axis of the blood inlet cover 19 (see FIGS. 4(a) and 4(b). In FIG. 4(a), the blood inlet chamber 28b has a maximum inside radius a, and the central axis X - X of the blood inlet cover 19 and the central axis Y - Y of the blood inlet port 26 are radially spaced from each other by a distance b. As shown in FIG. 4(a), the distance b is defined as the shortest distance between the axis X—X and Y—Y, i.e., wherein the line b intersects normally with both axis X—X and Y—Y. The blood inlet port 26 is radially offset from the central axis of the blood inlet cover 19 such that the ratio of the distance b to the radius a (hereinafter referred to as the "offset ratio") is in the range of from 0.25 to 0.95. The central axis of the blood inlet port 26 is oriented substantially perpendicularly to the axial direction of the pipes 23.

Figure 4B:
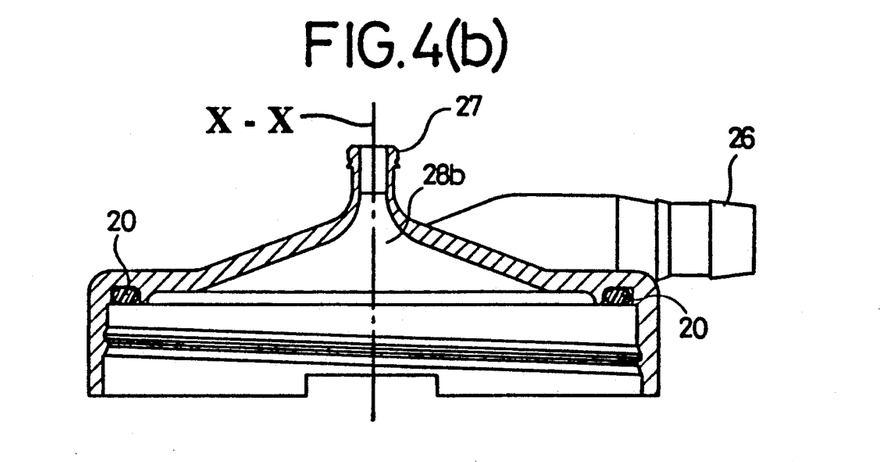

Blood which is introduced from the blood inlet port 26 is swirled in one direction in the blood inlet chamber 28b because the blood inlet port 26 is positionally displaced radially outwardly from the central axis of the blood inlet cover 19. The blood inlet cover 19 also has an air bleed port 27 defined substantially axially centrally thereof in communication with the blood inlet chamber 28b, for removing air bubbles which have been collected in the upper region of the blood inlet chamber 28b by the swirling blood stream.

Figure 5:
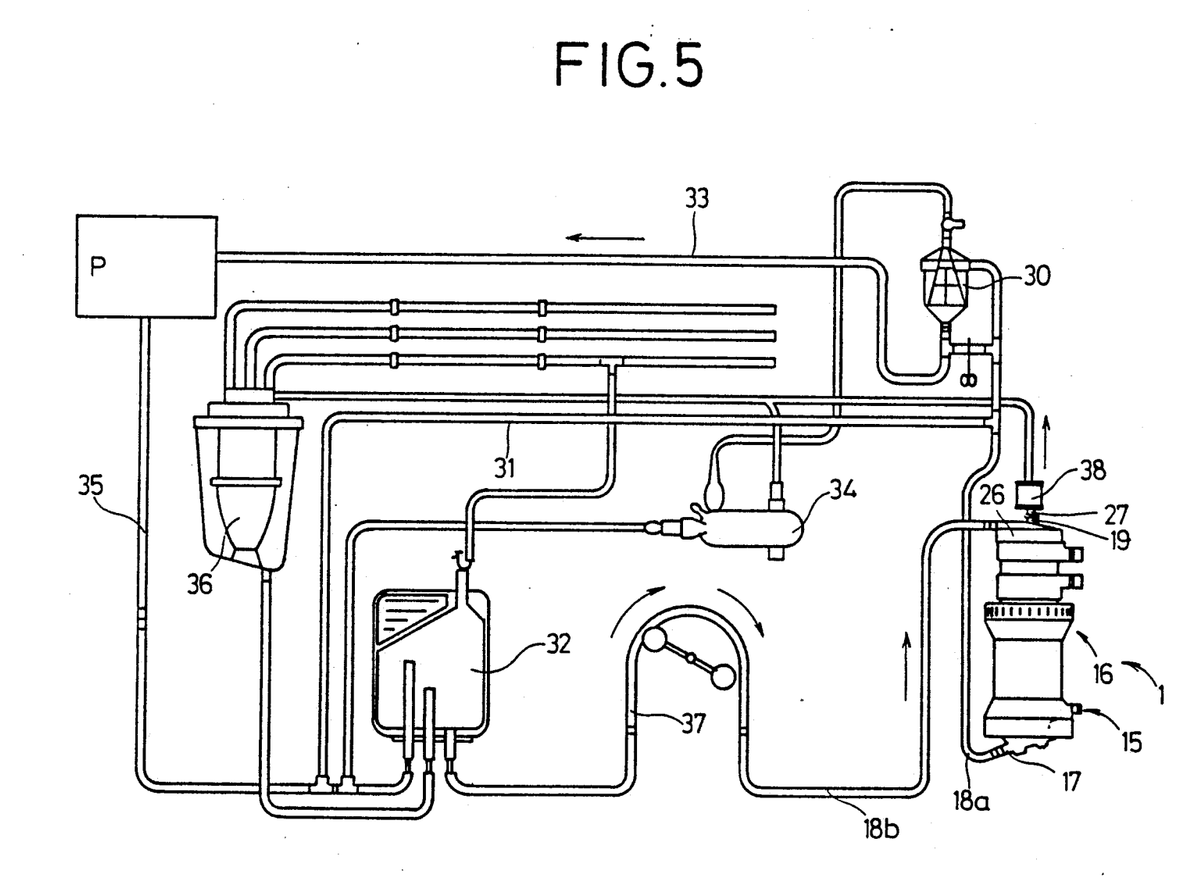
FIG. 5 is a circuit diagram of an extracorporeal blood circulation circuit incorporating the artificial lung assembly of the invention.

The artificial lung assembly 1 thus constructed is incorporated in an extracorporeal blood circulation circuit as shown in FIG. 5. The blood outlet port 17 of the artificial lung assembly 1 is connected through the tube 18a to a bubble trap 30 and a recirculation line 31 that is joined to a venous blood reservoir 32. The bubble trap 30 is coupled to a blood feed line 33 and a sampling manifold 34. The sampling manifold 34 is connected to the venous blood reservoir 32 and a cardiotomy reservoir 36 which is connected to the venous blood reservoir 32. The blood inlet port 26 is connected through a tube 18b and a roller pump 37 to the venous blood reservoir 32. The air bleed hole 27 of the blood inlet cover 19 is connected through a check valve 38 to the cardiotomy reservoir 36. The blood feed line 33 and a blood removal line 35 connected to the venous blood reservoir 32 are connected to a patient's body P.

The artificial lung assembly 1 operates as follows: First, the artificial lung assembly 1 is connected to the extracorporeal blood circulation circuit as shown in FIG. 5. Then, the extracorporeal blood circulation circuit is connected to the patient's body P who is to be subjected to cardiotomy or similar operation so that carbon dioxide will be removed from the blood of the patient and oxygen will be supplied to the blood. More specifically, during the operation, the blood removed from the vein of the patient's body P is delivered through the blood removal line 35 to the venous blood reservoir 32, from which the blood is forcibly fed under pressure by the pump 37 through the tube 18b into the blood inlet chamber 28b of the heat exchanger 3 from the blood inlet port 26 thereof. As described above, the blood inlet port 26 is positionally displaced radially outwardly from the central axis of the blood inlet cover 19 such that the offset ratio ranges from 0.25 to 0.95, and the axis of the blood inlet port 26 is oriented substantially perpendicularly to the axial direction of the pipes 23. Therefore, the blood which is entering from the blood inlet port 26 is swirled in one direction, and hence is dispersed in the blood inlet chamber 28b. The swirling blood flow does not directly impinge upon the open ends of the pipes 23, and hence almost no air bubbles are produced. Even if some air bubbles are produced in the blood in the blood inlet chamber 28b, since they are much smaller in mass than the blood, the air bubbles are collected centrally into the blood inlet chamber 28b under centripetal forces generated by the swirling blood flow. These collected air bubbles also move upwardly under buoyancy into the upper region of the blood inlet chamber 28b. The air bubbles are then discharged together with some blood through the air bleed hole 27 and flow through the check valve 38 into the cardiotomy reservoir 36. The cardiotomy reservoir 36 removes the air bubbles from the blood, and only the blood is delivered therefrom into the venous blood reservoir 32 for circulation.

The blood from which air bubbles have been removed in the manner described above and which has been dispersed in the blood inlet chamber 28b is then substantially uniformly distributed into the pipes 23 in the heat exchanger 3. A heat exchange is effected on the blood flowing through the pipes 23 by cold/warm water which enters from the thermal-medium inlet port 24 into the chamber 22 and is discharged from the chamber 22 through the thermal-medium outlet port 25. The blood then flows into the blood inlet chamber 9 of the artificial lung 2 and then into the hollow fiber membranes 14. The blood which is flowing through the hollow fiber membranes 14 is supplied with oxygen through the walls of the hollow fiber membranes 14 from a gas which contains oxygen and flows from the gas inlet port 15 into the gas chamber 13 and flows out of the gas chamber 13 through the gas outlet port 16. At the same time, carbon dioxide contained in the blood is removed and carried away by the gas which leaves the gas chamber 13. Thereafter, the blood flows from the hollow fiber membranes 14 into the blood outlet chamber 28a, from which it is drained from the blood outlet port 17 into the tube 18a. Since the blood outlet port 17 is inclined with respect to the axial direction of the hollow fiber membranes 14, the tube 18a connected to the blood outlet port 17 is not sharply bent. Accordingly, the artificial lung 1 can be located in a low position in the extracorporeal blood circulation circuit of FIG. 5, and hence the pressure of the blood therein is not excessively lowered. As a result, the gas containing oxygen does not enter the hollow fiber membranes 14, and no air bubbles are produced in the blood flowing through the hollow fiber membranes 14. The blood which has thus been oxygenated is then fed through the tube 18a and the bubble trap 30 to the blood feed line 33.

A comparative experiment conducted on the artificial lung assembly 1 according to the present invention and the conventional artificial lungs 1', 1" shown in FIGS. 1 and 2 will now be described with reference to FIGS. 6 through 10.

Figure 6:
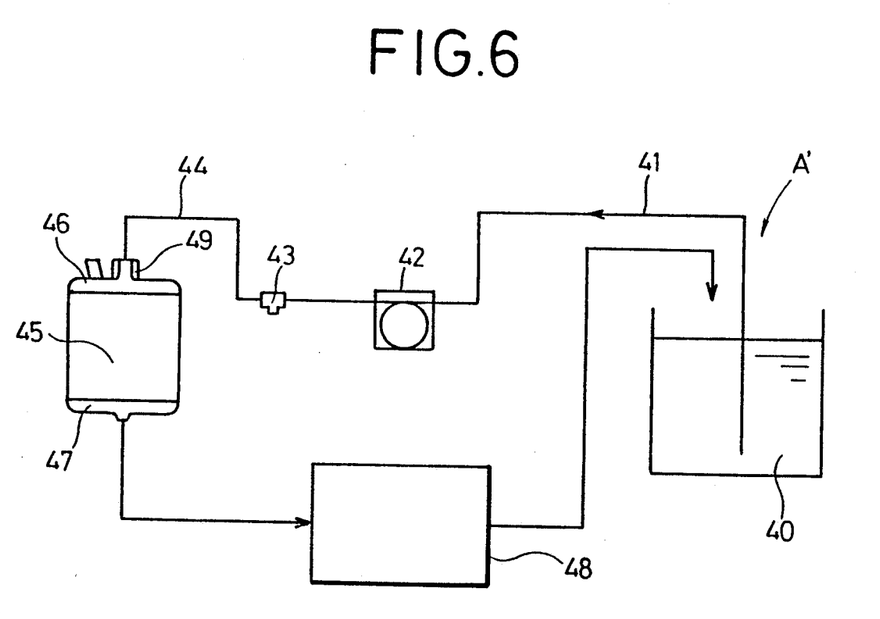
FIG. 6 is a circuit diagram of an experimental circuit for conducting comparative experiments.

As shown in FIG. 6, an experimental device or circuit A' has a blood reservoir tank 40 connected through a tube 41 to a roller pump 42. The roller pump 42 is connected to a blood inlet cover 46 of a heat exchanger 45 through a tube 44 which has an air bubble inlet port 43.

Figure 7A:
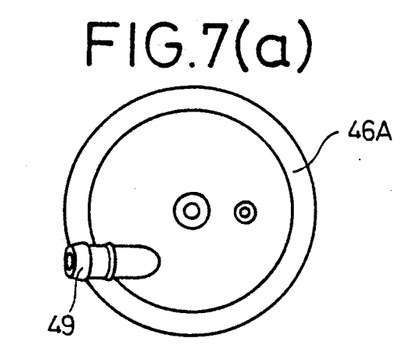
FIGS. 7(a) and 7(b) are plan and partly sectional side elevational views, respectively, of a blood inlet cover for use in a test according to the present invention.
Figure 7B:
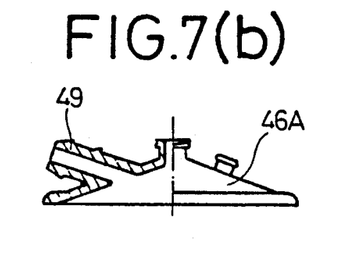
Figure 8A:
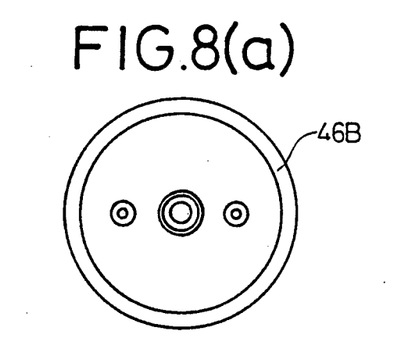
FIGS. 8(a) and 8(b) are plan and partly sectional side elevational views, respectively, of a conventional blood inlet cover for use in a test.
Figure 8B:
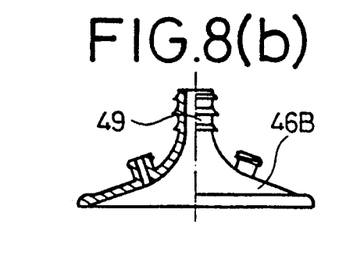
Figure 9A:
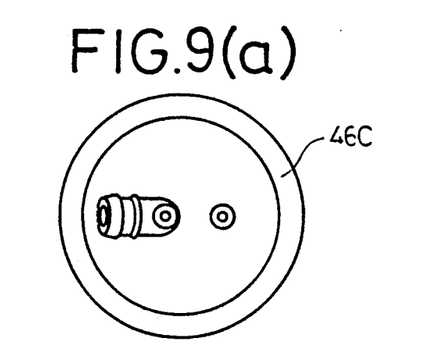
FIGS. 9(a) and 9(b) are plan and partly sectional side elevational views, respectively, of another conventional blood inlet cover for use in a test.
Figure 9B:
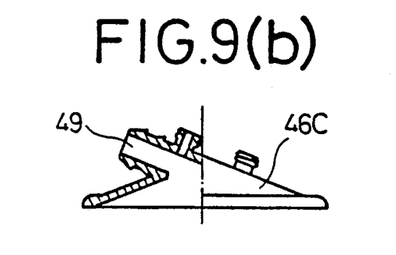

The, blood inlet cover 46, which is used for a test, is one of the blood inlet covers shown in FIGS. 7(a) and 7(b), 8(a) and 8(b), and 9(a) and (b). More specifically, FIGS. 7(a) and 7(b) show a blood inlet cover 46A for use in a test, which corresponds to the blood inlet cover 19 according to the present invention. FIGS. 8(a) and 8(b) show a straight-inlet-port blood inlet cover 46B for use in a test, which is employed in the conventional artificial lung 1'. The straight-inlet-port blood inlet cover 46B has a blood inlet port 49 extending along the axis of the cylindrical heat exchanger 45. FIGS. 9(a) and 9(b) show a lateral-inlet-port blood inlet cover 46C for use in a test, which is employed in the conventional artificial lung 1''. The lateral-inlet-port blood inlet cover 46C has a blood inlet port 49 inclined with respect to the central axis of the artificial lung 1''.

The heat exchanger 45 has a blood outlet cover 47 connected to an artificial lung 48 which is connected to the blood reservoir tank 40. In each of Inventive and Comparative Examples below, the blood inlet cover 46 had a blood inlet chamber 28b having an inside radius of 35.3 mm.

INVENTIVE EXAMPLE 1 AND COMPARATIVE EXAMPLES 1, 2

The distribution of pressures of blood flowing into the blood inlet chamber, i.e., the dispersion of blood in the blood inlet chamber, and the amount of air bubbles collected were measured with respect to the different blood inlet cover configurations. In Inventive Example 1, the blood inlet cover 46A was attached to the heat exchanger 45 of the experimental device A' shown in FIG. 6. Blood was delivered into the blood inlet cover 46A, and the pressures of the blood in the pipes in the heat exchanger 45 were measured at 61 locations. Air bubbles were introduced at the rate of 10 cc/min. into the blood in the tube 44 from the air bubble inlet port 43, and the blood was supplied to the blood inlet cover 46A by the roller pump 42 at the rates of 3.3 l/min., 4.3 l/min., and 5.4 l/min. The amount of air bubbles collected at this time were also measured. The influx of air bubbles into the heat exchanger pipes was visually confirmed through the blood outlet cover 47. The offset ratio of the blood inlet cover 46A in Inventive Example 1 was 0.68.

In Comparative Example 1, the blood inlet cover 46B was mounted on the heat exchanger 45, and in Comparative Example 2, the blood inlet cover 46C was mounted on the heat exchanger 45. The pressures of the blood and the amounts of collected air bubbles were measured in the same manner as with Inventive Example 1. The results of the measurements are given in the following Table 1:

TABLE 1

|  |  |  | In. Ex. 1 | Com. Ex. 1 | Com. Ex. 2 |
|---|---|---|---|---|---|
|  |  |  | mmAq | mmAq | mmAq |
| Pressure | σ (deviation score) |  | 1.7 | 2.8 | 3.8 |
|  | x (mean) |  | 48.9 | 44.9 | 50.8 |
| Total Distribution | σ/x × 100 |  | 3.5% | 6.3% | 7.4% |
|  | ΔP = max − min |  | 7 mmAq | 22 mmAq | 19 mmAq |
|  |  | l/min. | cc | cc | cc |
| Amount of collected | Blood flow | 3.3 | 10.0 | 6.6 | 8.8 |
|  |  | 4.3 | 10.0 | 6.7 | 7.8 |

TABLE 1-continued

|  | In. Ex. 1 | Com. Ex. 1 | Com. Ex. 2 |
|---|---|---|---|
| air bubbles rate 5.4 | 10.0 | 6.9 | 5.3 |

Table 1 shows that the pressure distribution according to Inventive Example 1 is most uniform, and it can be understood that the dispersion of the blood is better in Inventive Example 1. The amount of air bubbles collected in Inventive Example 1 is 100%, i.e., the air bubbles were almost entirely collected in Inventive Example 1.

INVENTIVE EXAMPLES 2, 3, 4 AND COMPARATIVE EXAMPLES 3, 4, 5

The dwell times of blood in the the blood inlet chamber, and the blood flow patterns in the blood inlet chamber were measured with respect to the different blood inlet cover configurations. In Inventive Example 2, the blood inlet cover 46A was attached to the heat exchanger 45 with the offset ratio being 0.28 (i.e., with the blood inlet port 49 being 10 mm displaced from the central axis of the blood inlet cover), and water was delivered into the blood inlet cover 46A through the blood inlet port 49 by the roller pump 42 at the rate of 3.3 l/min. 2.5 cc of blood was introduced into the tube 44 from the air bubble inlet port 43. The dwell time and the flow pattern of the blood in the blood inlet cover 46A were measured.

In Inventive Example 3, the blood inlet cover 46A was attached to the heat exchanger 45 with the offset ratio being 0.71 (i.e., with the blood inlet port 49 being 25 mm displaced from the central axis of the blood inlet cover).

In Inventive Example 4, the blood inlet cover 46A was attached to the heat exchanger 45 with the offset ratio being 0.93 (i.e., with the blood inlet port 49 being 33 mm displaced from the central axis of the blood inlet cover).

In Inventive Examples 3, 4, the dwell times and the flow patterns of the blood in the blood inlet cover 46A were measured in the same manner as with Inventive Example 2.

In Comparative Example 3, the blood inlet cover 46B was attached to the heat exchanger 45, and in Comparative Example 4, the blood inlet cover 46C was attached to the heat exchanger 45. The dwell times and the flow patterns of the blood in the blood inlet covers 46B, 46C were measured.

In Comparative Example 5, the blood inlet cover 46A was attached to the heat exchanger 45 with the offset ratio being 0.99 (i.e., with the blood inlet port 49 being 35 mm displaced from the central axis of the blood inlet cover).

Figure 10:
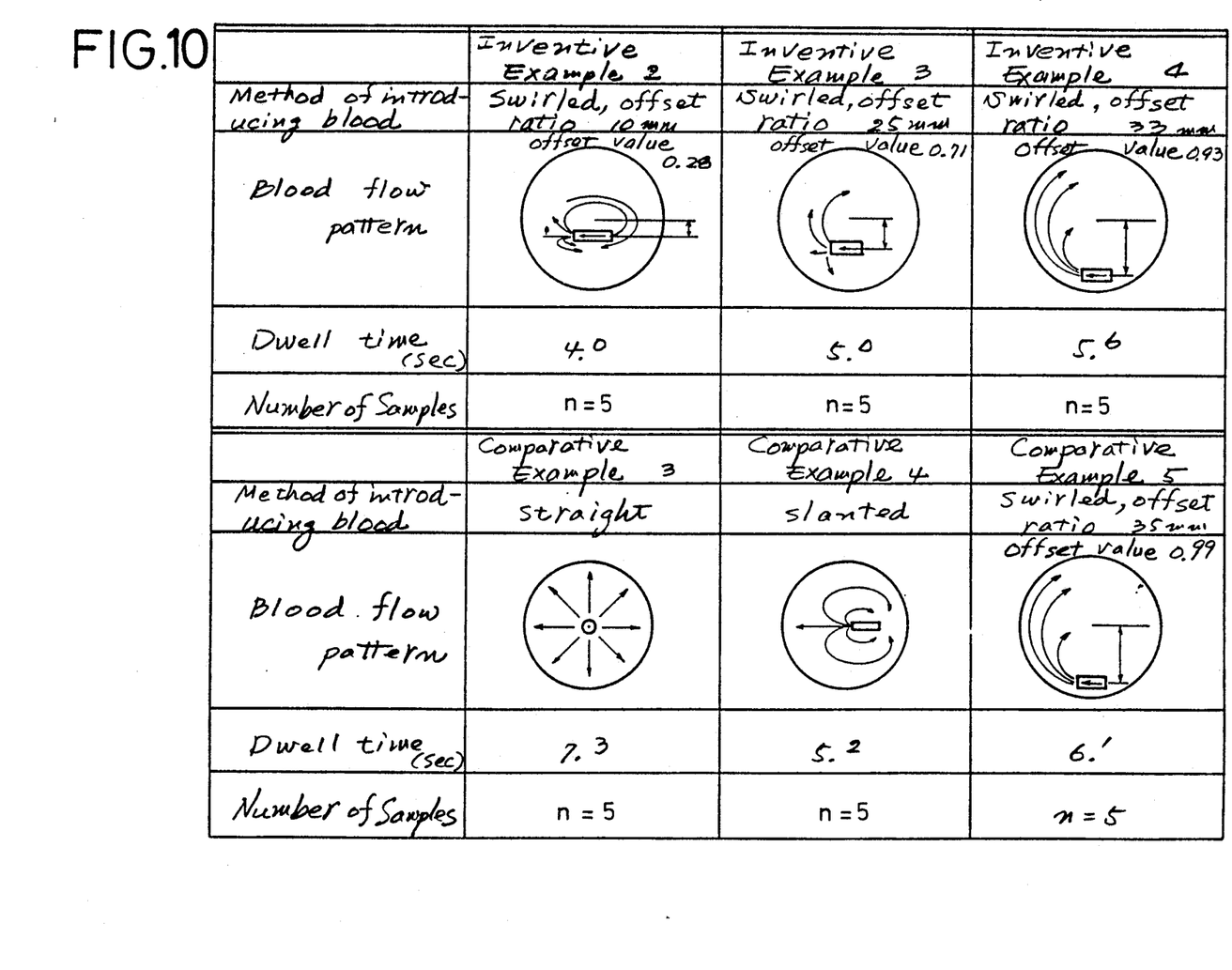
FIG. 10 is a diagram showing blood flow patterns, dwell times, and the numbers of samples in Inventive Examples 2 through 4 and Comparative Examples 3 through 5.

The results of the above measurements are shown in FIG. 10. It can be understood from FIG. 10 that the dwell time of the blood is shortest and air bubbles are prevented most easily from being produced in Inventive Example 2 in which the offset ratio is smallest.

INVENTIVE EXAMPLES 5, 6, 7 AND COMPARATIVE EXAMPLES 6, 7, 8

The uniformity of the speed of flow in the heat exchanger pipes was measured with respect to the different blood inlet cover configurations. In Inventive Example 5, the blood inlet cover 46A was attached to the heat exchanger 45 with the offset ratio being 0.28 as with Inventive Example 2. A solution containing 42% by weight of glycerin was supplied as pseudoblood to the blood inlet cover 46A by a centrifugal pump at the rate of 3.3 l/min., and the pressure of the solution on the upper surface of the heat exchanger 35 was measured. It is assumed that the pressure is proportional to the speed of flow in the heat exchanger pipes. Since the pressure to be measured was low, the column pressure of the glycerin solution was measured using an AVF (flanged intravenous needle).

In Inventive Example 6, the blood inlet cover 46A was attached to the heat exchanger 45 with the offset ratio being 0.68. The pressure on the upper surface of the heat exchanger 45 was measured in the same manner with Inventive Example 5 above.

In Inventive Example 7, the blood inlet cover 46A was attached to the heat exchanger 45 with the offset ratio being 0.93.

In Comparative Example 6, the blood inlet cover 46B was attached to the heat exchanger 45, and in Comparative Example 7, the blood inlet cover 46C was attached to the heat exchanger 45. In Comparative Example 8, the blood inlet cover 46A was attached to the heat exchanger 45 with the offset ratio being 0.15. The pressures on the upper surface of the heat exchanger 45 were measured in the same manner as with Inventive Example 5. The results of the measurements are shown in the following Table 2:

TABLE 2

|  | Pressure difference ΔP with surrounding area (water column in mm) |
| --- | --- |
| Inventive Example 5 | 8 |
| Inventive Example 6 | 3 |
| Inventive Example 7 | 4 |
| Comparative Example 6 | 34 |
| Comparative Example 7 | 28 |
| Comparative Example 8 | 15 |

Table 2 indicates that the pressure difference between the axial center and surrounding area in the blood inlet chamber is lower with Inventive Examples 5, 6, and 7. If the pressure is proportional to the speed of flow in the heat exchanger pipes, then it can be assumed that the pressure difference within the blood inlet chamber is lowest and the speed of flow in the pipes is uniform in Inventive Example 6 in particular.

INVENTIVE EXAMPLES 8, 9, 10 AND COMPARATIVE EXAMPLES 9, 10, 11

In these examples, the artificial lung assembly 1 was employed in which the heat exchanger 3 is positioned on top of the artificial lung 2, blood was introduced from the upper blood inlet cover 19 of the heat exchanger 3 and discharged from the lower blood outlet cover 10 of the artificial lung 2. The separability of air bubbles in these examples was measured with respect to the different blood inlet cover configurations. In Inventive Example 8, the blood inlet cover 46A was attached to the heat exchanger 45 with the offset ratio being 0.28 as with Inventive Example 2. In Inventive Example 9, the blood inlet cover 46A was attached to the heat exchanger 45 with the offset ratio being 0.68 as with Inventive Example 6. In Inventive Example 10, the blood inlet cover 46A was attached to the heat exchanger 45 with the offset ratio being 0.93 as with Inventive Example 4. First, the heat exchanger 45, i.e., the heat exchanger 3, was positioned beneath the artificial lung 2, water was introduced into the heat exchanger 3, and air bubbles were removed from the heat exchanger 45. Then, the artificial lung assembly 1 was turned upside down so that the heat exchanger 45 is positioned on top of the artificial lung 2. Air bubbles were admitted into the tube 44 through the air bubble inlet port 43, and those air bubbles were collected in the blood inlet cover 46A on the heat exchanger 45 by a syringe. The collected amounts of air bubbles were measured. 10 cc and 3 cc of air bubbles were introduced into the heat exchanger 45, and the water was supplied at the rates of 3.3 l/min., 4.3 l/min., and 5.4 l/min.

In Comparative Example 9, the blood inlet cover 46B was attached to the heat exchanger 45, and in Comparative Example 10, the blood inlet cover 46C was attached to the heat exchanger 45. In Comparative Example 11, the blood inlet cover 46A was attached to the heat exchanger 45 with the offset ratio being 0.15. The amounts of collected air bubbles were also measured. The results of the measurements are given in the following Table 3.

TABLE 3

| Water flow rate l/min. | Amount of added air bubbles cc | Amount of collected air bubbles | | | | | |
| --- | --- | --- | --- | --- | --- | --- | --- |
| | | Inventive Ex. | | | Comparative Ex. | | |
| | | 7 cc | 8 cc | 9 cc | 9 cc | 10 cc | 11 cc |
| 3.3 | 10 | 10.0 | 10.0 | 10.0 | 9.4 | 8.4 | 9.7 |
| 4.3 | 10 | 9.6 | 9.8 | 9.8 | 9.6 | 9.0 | 9.6 |
| 5.4 | 10 | 9.0 | 9.8 | 9.6 | 8.6 | 9.0 | 9.0 |
| 3.3 | 3 | 3.0 | 3.0 | 3.0 | 2.6 | 1.8 | 3.0 |
| 4.3 | 3 | 3.0 | 3.0 | 3.0 | 2.4 | 2.2 | 2.8 |
| 5.4 | 3 | 2.6 | 3.0 | 3.0 | 2.0 | 2.3 | 2.6 |

Table 3 shows that air bubbles can well be removed even if the artificial lung assembly is turned upside down as with the present invention.

In view of the removal of air bubbles and the pressure difference between the axial center of the blood inlet cover 46 and the surrounding area around the axial center thereof based on the experimental results of Inventive Examples 2 through 9, it has been found that the offset ratio, i.e., the ratio of the distance from the central axis of the blood inlet cover 46 to the central axis of the blood inlet port 49 to the inside radius of the blood inlet chamber, should preferably be in the range of from 0.25 to 0.95, more preferably be in the range of from 0.30 to 0.90, and much more preferably be in the range of from 0.50 to 0.85.

If the offset ratio were smaller than 0.25, the pressure difference between the axial center of the blood inlet cover 46 and the surrounding area thereof would be so high that the amount of blood would differ in the axial center and surrounding of the blood inlet cover 46. As a result, heat and gas exchanges would be ineffective, and air bubbles would not effectively be removed as an effective swirling blood stream would not be produced.

If the offset ratio were greater than 0.95, the dwell time of blood in the blood inlet cover 46 would be longer, and its ability to remove air bubbles would be lowered.

While the artificial lung assembly 1 of the present invention includes a heat exchanger, the present invention is also applicable to an artificial lung which is not associated with a heat exchanger.

With the present invention, the blood inlet port of the blood inlet cover is positioned such that the ratio of the distance from the central axis of the blood inlet cover to the central axis of the blood inlet port to the inside radius of the blood inlet chamber ranges from 0.25 to 0.95, so that the blood introduced from the blood inlet port into the blood inlet chamber will be swirled in one direction. Therefore, the blood which flows from the blood inlet port into the blood inlet chamber is swirled in one direction, and hence is uniformly dispersed in the blood inlet chamber. Since the uniformly dispersed blood does not directly impinge upon the ends of the hollow fiber membranes, air bubbles produced in the blood are very few. Any air bubbles which are generated in he blood inlet chamber are directed toward the center of the blood inlet chamber under centripetal forces caused by the swirling blood stream since the air bubbles are much smaller in mass than the blood. The air bubbles are also moved upwardly under buoyancy and separated from the blood in the blood inlet chamber. Therefore, the blood can uniformly be supplied into the artificial lung without air bubbles trapped therein. Since any air bubbles have been removed from the blood in the heat exchanger, the blood supplied from the artificial lung is substantially free from air bubbles. The air bubbles collected in the upper region in the blood inlet chamber are discharged out of the blood inlet cover through the air bleed port defined substantially axially centrally in the blood inlet cover. Consequently, the air bubbles trapped in the blood as it enters the heat exchanger can easily be discharged therefrom through the air bleed port.

The pressure difference between the axial center and surrounding area in the blood inlet chamber is small, allowing the blood to be distributed uniformly into the hollow fiber membranes. Accordingly, an exchange of a gas such as oxygen can efficiently be effected between the blood and the gas flowing around the hollow fiber membranes. Since the dwell time of the blood in the blood inlet chamber is shortened, the ability of the blood inlet cover to remove air bubbles is high.

The heat exchanger is mounted on top of the artificial lung, and the blood inlet port of the blood inlet cover of the heat exchanger is positioned such that the ratio of the distance from the central axis of the blood inlet cover to the central axis of the blood inlet port to the inside radius of the blood inlet chamber ranges from 0.25 to 0.95, so that the blood introduced from the blood inlet port into the blood inlet chamber will be swirled in one direction. Therefore, the blood which flows from the blood inlet port into the blood inlet chamber is swirled in one direction, and hence is uniformly dispersed in the blood inlet chamber. Since the uniformly dispersed blood does not directly impinge upon the ends of the hollow fiber membranes, air bubbles produced in the blood are very few. Any air bubbles which are generated in the blood inlet chamber are directed toward the center of the blood inlet chamber under centripetal forces caused by the swirling blood stream since the air bubbles are much smaller in mass than the blood. The air bubbles are also moved upwardly under buoyancy and separated from the blood in the blood inlet chamber. Therefore, in the artificial lung assembly with the heat exchanger mounted on top of the artificial lung, the blood can uniformly be supplied into the artificial lung without air bubbles trapped therein. Since the air bubbles have been removed from the blood in the heat exchanger, the blood supplied from the artificial lung is substantially free from air bubbles.

The pressure difference between the axial center and surrounding area in the blood inlet chamber is small, allowing the blood to be distributed uniformly into the heat exchanger pipes and the hollow fiber membranes. Accordingly, an exchange of heat and a gas such as oxygen can efficiently be effected between the blood and air and also between the blood and the gas flowing around the hollow fiber membranes. Since the dwell time of the blood in the blood inlet chamber is shortened, the ability of the blood inlet cover to remove air bubbles is high.

Although a certain preferred embodiment has been shown and described, it should be understood that many changes and modifications may be made therein without departing from the scope of the appended claims.

What is claimed is:

1. An artificial lung comprising:
   a housing having means defining gas inlet and outlet ports and defining a gas flow path through said housing between said gas inlet and outlet ports;
   a first partition disposed in an upper end of said housing;
   a blood inlet chamber at said upper end of said housing and defined between said first partition and a blood inlet cover disposed above said first partition, said blood inlet cover having a tapered surface converging upwardly toward a central axis of said blood inlet chamber, wherein said blood inlet chamber defines a conically shaped volume into which the blood is introduced;
   a second partition disposed in a lower end of said housing;
   a blood outlet chamber at said lower end of said housing and defined below said second partition;
   a plurality of hollow fiber membranes for exchanging a gas, disposed within said housing and having ends opening into said blood inlet chamber and opposite ends opening into said blood outlet chamber;
   means defining a blood inlet port comprising a tubular member having a central axis, said inlet port communicating with said blood inlet chamber and positioned such that one end of said tubular member joins said blood inlet cover along said tapered surface at a position between the central axis of said blood inlet chamber and an inner circumference of said blood inlet chamber, wherein the ratio of the shortest, measured in a cross-sectional direction, from the central axis of said blood inlet chamber to the central axis of said tubular member, to an inside radius of said blood inlet chamber, ranges from 0.25 to 0.95, such that blood introduced from said blood inlet port into said blood inlet chamber will be swirled in one direction; and
   means defining an air bleed port positioned substantially axially centrally in said blood inlet chamber and communicating with said blood inlet chamber.

2. An artificial lung according to claim 1, wherein said ratio ranges from 0.30 to 0.90.

3. An artificial lung according to claim 1, wherein said ratio ranges from 0.50 to 0.85.

4. An artificial lung assembly comprising an artificial lung and heat exchanger in combination, comprising:
   an artificial lung housing having means defining gas inlet and outlet ports, and defining a gas flow path through said housing between said gas inlet and outlet ports;
   a first partition disposed in an upper end of said artificial lung housing;
   a first blood inlet chamber at said upper end of said artificial lung housing and defined above said first partition;

a second partition disposed in a lower end of said artificial lung housing;

a blood outlet chamber at said lower end of said artificial lung housing and defined below said second partition; and a plurality of hollow fiber membranes for exchanging a gas, disposed within said artificial lung housing and having ends opening into said first blood inlet chamber and opposite ends opening into said blood outlet chamber; and wherein said heat exchanger is mounted on said upper end of said artificial lung housing, said heat exchanger comprising:

a heat exchanger housing having means defining thermal medium inlet and outlet ports;

a third partition disposed in an upper end of said heat exchanger housing;

a second blood inlet chamber at said upper end of said heat exchanger housing and defined between said third partition and a blood inlet cover disposed above said third partition, said blood inlet cover having a tapered surface converging upwardly toward a central axis of said second blood inlet chamber, wherein said second blood inlet chamber defines a conically shaped volume into which the blood is introduced;

a fourth partition disposed in a lower end of said heat exchanger housing and facing into said first blood inlet chamber;

a plurality of pipes for exchanging heat, disposed within said heat exchanger housing and having ends opening into said second blood inlet chamber and opposite ends opening into said first blood inlet chamber;

means defining a blood inlet port comprising a tubular member having a central axis, said inlet port communicating with said second blood inlet chamber and positioned such that one end of said tubular member joins said second blood inlet cover along said tapered surface at a position between the central axis of said second blood inlet chamber and an inner circumference of said second blood inlet chamber, wherein the ratio of the shortest distance, measured in a cross-sectional direction, from the central axis of said second blood inlet chamber to the central axis of said tubular member, to the inside radius of said second blood inlet chamber, ranges from 0.25 to 0.95, such that blood introduced from said blood inlet port into said second blood inlet chamber will be swirled in one direction; and means defining an air bleed port positioned substantially axially centrally in said first blood inlet chamber and communicating with said first blood chamber.

5. An artificial lung according to claim 4, wherein said ratio ranges from 0.30 to 0.90.

6. An artificial lung according to claim 4, wherein said ratio ranges from 0.50 to 0.85.

* * * * *

UNITED STATES PATENT AND TRADEMARK OFFICE
CERTIFICATE OF CORRECTION

PATENT NO. : 5,084,244
DATED : January 28, 1992
INVENTOR(S) : T. MURAMOTO

It is certified that error appears in the above-identified patent and that said Letters Patent is hereby corrected as shown below:

Column 8, line 8, change "most uniform" to read
--mostly uniform--.

Column 12, line 44 (claim 1), after "shortest", insert
--distance--.

Signed and Sealed this

Thirteenth Day of July, 1993

Attest:

MICHAEL K. KIRK

Attesting Officer      Acting Commissioner of Patents and Trademarks